United States Patent [19]

Miyazaki et al.

[11] Patent Number: 4,551,565
[45] Date of Patent: Nov. 5, 1985

[54] PROCESS FOR THE PRODUCTION OF ETHYLENE GLYCOL AND/OR GLYCOLLIC ACID ESTERS, AND CATALYST THEREFOR

[75] Inventors: Haruhiko Miyazaki; Koichi Hirai; Taizo Uda; Yasuo Nakamura, all of Ube; Harumi Ikezawa, Onoda; Takanori Tsuchie, Ube, all of Japan

[73] Assignee: UBE Industries, Ltd., Yamaguchi, Japan

[21] Appl. No.: 510,387

[22] Filed: Jul. 5, 1983

Related U.S. Application Data

[63] Continuation of Ser. No. 341,237, Jan. 21, 1982, abandoned.

[30] Foreign Application Priority Data

Jan. 26, 1981 [JP] Japan .................................. 56-9059

[51] Int. Cl.$^4$ ........................................... C07C 29/136
[52] U.S. Cl. .................................... 568/864; 560/179
[58] Field of Search ........................ 560/179; 568/864

[56] References Cited

U.S. PATENT DOCUMENTS

| 2,091,800 | 8/1937 | Adkins et al. | 568/564 |
| 4,087,470 | 5/1978 | Suzuki | 568/564 |
| 4,112,245 | 9/1978 | Zehner | 568/564 |

Primary Examiner—Natalie Trousof
Assistant Examiner—L. Hendriksen
Attorney, Agent, or Firm—Sherman & Shalloway

[57] ABSTRACT

In a process for producing ethylene glycol and/or a glycollic acid ester by the vapor phase catalytic hydrogenation of an oxalic acid diester in the presence of a catalyst and hydrogen gas, the improvement wherein the catalyst has the following composition formula $$CuMo_kBa_pO_q$$

wherein k, p and q represent gram-atoms of Mo, Ba and O, respectively, per gram-atom of Cu, k is a number of from 0 to 3, p is a number of from 0 to 6, and q is a number determined depending upon the atomic valence and gram-atoms of Cu, Mo and Ba, provided that k and p are not zero at the same time; and the aforesaid catalyst.

11 Claims, No Drawings

PROCESS FOR THE PRODUCTION OF ETHYLENE GLYCOL AND/OR GLYCOLLIC ACID ESTERS, AND CATALYST THEREFOR

This application is a continuation, of application Ser. No. 341,237, filed Jan. 21, 1982, now abandoned.

This invention relates to an improved process for producing ethylene glycol and/or a glycollic acid ester by the vapor (or gaseous) phase catalytic hydrogenation of an oxalic acid diester in the presence of a catalyst and hydrogen gas, and to a catalyst for use in the process. The catalyst has excellent performance comparable to that of conventional copper chromite type catalysts, and the process of this invention is free from the troubles associated with the treatment of the conventional chromium-containing catalysts after use, especially the toxic hazard of chromium. Furthermore, the process can give either ethylene glycol or glycollic acid esters selectively depending upon the reaction conditions employed.

More specifically, this invention pertains, in a process for producing ethylene glycol and/or a glycollic acid ester by the vapor phase catalytic hydrogenation of an oxalic acid diester in the presence of a catalyst and hydrogen gas, to the improvement wherein the catalyst has the following composition formula $$CuMo_kBa_pO_q \qquad (1)$$

wherein k, p and q represent gram-atoms of Mo, Ba and O, respectively, per gram-atom of Cu, k is a number of from 0 to 3, p is a number of from 0 to 6 and q is a number determined depending upon the atomic valences and gram-atoms of Cu, Mo and Ba, provided that k and p are not zero at the same time. The invention also relates to the aforesaid catalyst.

A process for the production of ethylene glycol and glycollic acid esters by vapor phase catalytic hydrogenation of oxalate esters, such as dibutyl oxalate, at an elevated temperature in the presence of a hydrogenation catalyst, such as a copper chromite type catalyst, and hydrogen gas is known, for example, from U.S. Pat. No. 4,112,245 (corresponding to Japanese Patent Publication No. 42971/80), and German Pat. No. 459,603. The U.S. Patent states that in the process disclosed therein, hydrogenation catalysts containing copper either in the elementary form or combined with oxygen, as well as other hydrogenating metal oxides employed in conjunction with copper, supported or unsupported, may generally be used, and that especially preferred catalysts are the copper zinc chromite or copper chromite catalysts which may be promoted with barium or sodium hydroxide and which have been reduced in hydrogen. The working examples of this U.S. Patent disclose the use of copper zinc chromite, barium-promoted copper chromite, sodium hydroxide-promoted copper chromite and copper chromite catalysts.

These previously recommended copper chromite-type catalysts have excellent catalytic performance, but since they cause troubles in industrial operations, their practical value is extremely reduced. Specifically, chromium is an essential ingredient of catalysts of the above type, but it is extremely difficult to recover chromium completely from spent catalysts with good efficiency. As is well known, chromium even in trace amounts shows strong toxicity to humans, and the discarding of the spent catalysts containing chromium causes serious environmental pollution.

On the other hand, various general hydrogenation catalysts other than those of the copper chromite type are known. Examples include metal catalysts such as Raney nickel, cobalt, copper, iron, platinum, and palladium, and the oxides and sulfides of these metals. It is well known however that these general hydrogenation catalysts do not always show practical utility in all catalytic hydrogenation reactions, and unless a catalyst is selected which conforms to many different factors such as the mode and mechanism of a given reaction, the reaction conditions, etc., the desired reaction cannot be carried out with good efficiency, and moreover that there is no established guideline for the selection of such a catalyst.

The present inventors have worked extensively in order to provide a catalyst free from the troubles of the aforesaid copper chromite-type catalysts in the production of ethylene glycol and/or a glycollic acid ester by the vapor phase catalytic hydrogenation reaction of an oxalic acid diester. As a result, they found that a novel catalyst substantially free from chromium and having the composition formula (1) given hereinabove has excellent catalytic performance comparable to that of the copper chromite type catalytes in the aforesaid particular reaction, and does not require treatment after use unlike the copper chromite type catalysts, and that the use of this novel catalyst makes it possible to form either ethylene glycol or glycollic acid esters selectively depending upon the reaction conditions used.

It is an object of this invention therefore to provide an improved process for producing ethylene glycol and/or a glycollic acid ester by the vapor-phase catalytic hydrogenation of an oxalic acid diester.

Another object of this invention is to provide a novel catalyst for the vapor phase catalytic hydrogenation of an oxalic acid diester.

The above and other objects and advantages of this invention will become apparent from the following description.

The catalyst in accordance with this invention has the following composition formula $$CuMo_kBa_pO_q \qquad (1)$$

wherein k, p and q represent gram-atoms of Mo, Ba and O, respectively, per gram-atom of Cu, k is a number of from 0 to 3, p is a number of from 0 to 6, and q is a number determined depending upon the atomic valences and gram-atoms of Cu, Mo and Ba, provided that k and p are not zero at the same time.

The catalyst of this invention having the composition formula (1) above can be prepared, for example, by the following procedure.

A water-soluble copper compound such as cupric nitrate is dissolved in water to form an aqueous solution containing a copper ion, and the aqueous solution is added to an aqueous solution of an alkalizing agent such as an aqueous solution of sodium hydroxide to form a precipitate. The precipitate is collected by a suitable solid-liquid separating means such as filtration, and washed fully with water. The above operation of precipitate formation can be carried out at room temperature, and cooling or heating is not particularly required. For example, it may be carried out at a temperature of about 30° to about 90° C. The resulting cake-like solid is admixed with the desired calculated amounts of a molybdenum compound such as molybdic acid and/or a barium compound such as barium hydroxide. If desired, a small amount of water is further added. These are mixed and milled for a period of, for example, about 2 hours to about 20 hours. The treated product is dried for a period of about 10 to about 20 hours. The resulting catalyst may be used in the vapor phase catalytic hydrogenation of an oxalic acid diester according to this invention after it is subjected to reducing treatment. The reducing treatment can be carried out, for example, in a hydrogen stream at a temperature of, for example, about 160° to 250° C., for a period of, for example, about 0.5 to about 5 hours.

The copper compound (including copper salts) used in the catalyst preparation may be any water-soluble copper compound. Examples include copper nitrate, copper sulfate, copper chloride, copper oxalate and copper acetate. Cupric nitrate is especially preferred. The aqueous solution containing an alkalizing agent is, for example, an aqueous solution of an alkali such as sodium hydroxide, potassium hydroxide, and sodium carbonate, but is not limited thereto. Preferably, the alkalizing agent is used in an amount sufficient to precipitate a copper ion substantially completely.

Sources of molybdenum and barium which are used in the above catalyst preparation may include molybdic acid ($H_2MoO_4$), barium hydroxide [$Ba(OH)_2$], ammonium molybdate, molybdenum oxide, barium oxide, and barium molybdate which contains both Mo and Ba. These specific names of compounds are given only for the purpose of illustration.

According to the process of this invention, an oxalic acid diester is catalytically hydrogenated in the vapor phase in the presence of the aforesaid catalyst.

Preferred examples of the starting oxalate are di($C_1$–$C_8$)-alkyl esters of oxalic acid, specifically dimethyl oxalate, diethyl oxalate, dibutyl oxalate, diamyl oxalate, etc.

The known reaction conditions disclosed, for example, in the above cited U.S. Pat. No. 4,112,245 (corresponding to Japanese Patent Publication No. 42971/1980), German Pat. No. 459,603, and British Pat. No. 2,031,883 (corresponding to Japanese Laid-Open Patent Publication No. 40685/1980) can be properly selected for the practice of the process of the present invention. The preferred reaction conditions for the vapor phase catalytic hydrogenation in the presence of the catalyst of this invention are as follows:

Temperature: about 120° to about 300° C., preferably about 150° to about 240° C.
Contact time: about 0.01 to about 20 seconds, preferably about 0.2 to about 6 seconds
pressure: about 0.1 to about 200 atmospheres, preferably about 0.5 to about 50 atmospheres,
Hydrogen/oxalate mole ratio: at least about 2, preferably about 10 to about 500

Generally, both ethylene glycol and a glycollic acid ester can be formed by the vapor phase catalytic hydrogenation of an oxalic acid diester in the presence of the catalyst having the composition formula (1). Ethylene glycol is formed at a high selectivity when k+p is not more than 2 and the ratio of k to p is within the range of from 0.5 to 2 in the catalyst (namely when the total gram-atoms of molybdenum and barium atoms in the catalyst are not more than two times the gram-atoms of copper and the ratio of the gram-atoms of the molybdenum atom to the gram-atoms of the barium atom is from 0.5 to 2). This tendency becomes especially remarkable when k+p is 1.5 or below and the k/p ratio is about 1, for example 0.8 to 1.2.

When the reaction pressure in the vapor phase catalytic hydrogenation in the presence of the catalyst of this invention is present at a relatively low value (for example, at 0.5 to 3 atmospheres), the glycollate tends to be formed in a relatively large amount. Conversely, when it is prescribed at a higher value (for example, more than 3 atmospheres), ethylene glycol tends to be formed in a relatively large amount.

The ratio between ethylene glycol and the glycollate in the reaction product obtained by the hydrogenation reaction of the oxalate in the presence of the catalyst of this invention shows the aforesaid tendency according to the proportions of the catalyst ingredients and the reaction pressure. Hence, the ratio between the components of the reaction product can be varied as desired by properly selecting and presetting these conditions. Furthermore, it is possible to obtain substantially only one of ethylene glycol and glycollate selectively.

The following examples illustrate the present invention more specifically.

EXAMPLE 1

One hundred grams of cupric nitrate trihydrate [$Cu(NO_3)_2 \cdot 3H_2O$] was dissolved in 400 ml of water. The aqueous solution was added to 300 ml of an aqueous solution of sodium hydroxide at about 80° C. (prepared by dissolving 35 g of sodium hydroxide in 300 ml of water) to form a precipitate at about 80° C. Th precipitate was collected by filtration, and fully washed with water to form a cake-like solid. Molybdic acid (0.83 g) and 1.7 g of barium hydroxide were added to the solid, and then a small amount of water was added. They were fully mixed and milled for 16 hours. The resulting mixture was dried at about 140° C. for 12 hours. In the resulting catalyst, the Cu:Mo:Ba atomic ratio was 1:0.01:0.01.

1.0 g of the resulting catalyst was taken, and filled in a stainless steel reaction tube (4 mm in inside diameter). While the catalyst in the reaction tube was heated at 200° C., hydrogen gas was passed through the catalyst for 4 hours to reduce the catalyst. Diethyl oxalate was hydrogenated in the reaction tube at each of the temperatures shown in Table 1 under atmospheric pressure with a contact time of 1.5 g.second/ml. The hydrogen/diethyl oxalate mole rate in the feed was set at 200. The results are shown in Table 1.

TABLE 1

| Reaction temperature (°C.) | Conversion of diethyl oxalate (%) | Selectivity to ethylene glycol (%) | Selectivity to ethyl glycollate (%) |
| --- | --- | --- | --- |
| 190 | 100 | 89.9 | 0.7 |
| 180 | 100 | 86.7 | 3.0 |

EXAMPLE 2

A catalyst in which the Cu:Mo:Ba ratio atomic ratio was 1:0.06:0.06 was prepared in the same way as in Example 1 except that the amounts of molybdic acid and barium hydroxide were changed. Diethyl oxalate was hydrogenated under the same conditions as in Example 1 except that the resulting catalyst was used, and the reaction temperature was varied as shown in Table 2. The results are shown in Table 2.

TABLE 2

| Reaction temperature (°C.) | Conversion of diethyl oxalate (%) | Selectivity to ethylene glycol (%) | Selectivity to ethyl glycollate (%) |
| --- | --- | --- | --- |
| 193 | 100 | 93.4 | 1.0 |
| 175 | 99.5 | 87.2 | 7.8 |

EXAMPLE 3

A catalyst in which the atomic ratio of Cu:Mo:Ba was 1:0.1:0.1 was prepared in the same way as in Example 1 except that the amounts of molybdic acid and barium hydroxide were changed. Diethyl oxalate was hydrogenated under the same conditions as in Example 1 except that the resulting catalyst was used, and the reaction temperature was changed as shown in Table 3.

TABLE 3

| Reaction temperature (°C.) | Conversion of diethyl oxalate (%) | Selectivity to ethylene glycol (%) | Selectivity to ethyl glycollate (%) |
| --- | --- | --- | --- |
| 180 | 100 | 91.1 | 0.8 |
| 170 | 100 | 75.4 | 21.3 |

EXAMPLE 4

A catalyst in which the atomic ratio of Cu:Mo:Ba was 1:0.2:0.2 was prepared in the same way as in Example 1 except that the amounts of molybdic acid and barium hydroxide were changed. Diethyl oxalate was hydrogenated under the samd conditions as in Example 1 except that the resulting catalyst was used and the reaction temperature was changed as shown in Table 4. The results are shown in Table 4.

TABLE 4

| Reaction temperature (°C.) | Conversion of diethyl oxalate (%) | Selectivity to ethylene glycol (%) | Selectivity to ethyl glycollate (%) |
| --- | --- | --- | --- |
| 190 | 100 | 87.0 | 0 |
| 185 | 100 | 93.9 | 0 |
| 177 | 100 | 97.7 | 1.2 |

EXAMPLE 5

A catalyst in which the Cu:Mo:Ba atomic ratio was 1:0.5:0.5 was prepared in the same way as in Example 1 except that the amounts of molybdic acid and barium hydroxide were changed. Diethyl oxalate was hydrogenated under the same conditions as in Example 1 except that the resulting catalyst was used and the reaction temperature was changed as shown in Table 5. The results are shown in Table 5.

TABLE 5

| Reaction temperature (°C.) | Conversion of diethyl oxalate (%) | Selectivity to ethylene glycol (%) | Selectivity to ethyl glycollate (%) |
| --- | --- | --- | --- |
| 200 | 98.3 | 47.5 | 50.6 |
| 210 | 100 | 74.1 | 20.9 |
| 220 | 100 | 73.9 | 6.1 |
| 210* | 100 | 80.1 | 1.9 |
| 200* | 100 | 63.2 | 26.8 |

The reactions at the asterisked temperatures were carried out with a contact time of 3.0 g.sec/ml.

EXAMPLE 6

A catalyst in which the Cu:Mo:Ba atomic ratio was 1:2:2 was prepared in the same way as in Example 1 except that the amounts of molybdic acid and barium hydroxide were changed. Diethyl oxalate was hydrogenated under the same conditions as in Example 1 except that the resulting catalyst was used and the reaction temperature was changed as shown in Table 6. The results are shown in Table 6.

TABLE 6

| Reaction temperature (°C.) | Conversion of diethyl oxalate (%) | Selectivity to ethylene glycol (%) | Selectivity to ethyl glycollate (%) |
| --- | --- | --- | --- |
| 210 | 46.4 | 0 | 88.1 |
| 220* | 53.6 | 0 | 83.2 |
| 240* | 81.4 | 0 | 75.6 |

The reactions at the asterisked temperatures were carried out with a contact time of 3.0 g.sec/ml.

EXAMPLE 7

A catalyst in which the Cu:Mo:Ba atomic ratio was 1:0.2:0.01 was prepared in the same way as in Example 1 except that the amounts of molybdic acid and barium hydroxide were changed. Diethyl oxalate was hydrogenated under the same conditions as in Example 1 except that the resulting catalyst was used and the reaction temperature was changed as shown in Table 7. The results are shown in Table 7.

TABLE 7

| Reaction temperature (°C.) | Conversion of diethyl oxalate (%) | Selectivity to ethylene glycol (%) | Selectivity to ethyl glycollate (%) |
| --- | --- | --- | --- |
| 190 | 96.3 | 0 | 77.1 |
| 185 | 85.3 | 0 | 80.3 |

EXAMPLE 8

A catalyst in which the Cu:Mo:Ba atomic ratio of 1:0.01:0.2 was prepared in the same way as in Example 1 except that the amounts of molybdic acid and barium hydroxide were changed. Diethyl oxalate was hydrogenated under the same conditions as in Example 1 except that the resulting catalyst was used and the reaction temperature was changed to 193° C.

Analysis of the products in the early stage of the reaction showed a diethyl oxalate conversion of 99.6%, an ethylene glycol selectivity of 85.9%, and an ethyl glycollate selectively of 16.2%.

EXAMPLE 9

A catalyst in which the Cu:Mo atomic ratio was 1:0.2 was prepared in the same way as in Example 1 except that the amount of molybdic acid was changed and barium hydroxide was not added. Diethyl oxalate was hydrogenated under the same conditions as in Example 1 except that the resulting catalyst was used and the reaction temperature was changed as shown in Table 8. The results are shown in Table 8.

TABLE 8

| Reaction temperature (°C.) | Conversion of diethyl oxalate (%) | Selectivity to ethylene glycol (%) | Selectivity to ethyl glycollate (%) |
| --- | --- | --- | --- |
| 200 | 54.4 | 0 | 91.3 |
| 210 | 84.4 | 0 | 86.2 |
| 218 | 94.6 | 0 | 81.7 |

EXAMPLE 10

A catalyst in which the atomic ratio of Cu:Ba was 1:0.2 was prepared in the same way as in Example 1 except that the amount of barium hydroxide was changed and molybdic acid was not added.

Diethyl oxalate was hydrogenated under the same conditions as in Example 1 except that the resulting catalyst was used and the reaction temperature was changed to 190° C.

Analysis of the reaction poducts in the early stage of the reaction showed a diethyl oxalate conversion of 73.6%, an ethylene glycol selectivity of 53.7%, and an ethyl glycollate selectivity of 31.2%.

EXAMPLES 11 TO 14

Ten milliliters (12.1 g) of the catalyst prepared in Example 4 was taken, and filled in a stainless steel reaction tube (10 mm in inside diameter). The catalyst was then subjected to a reducing treatment under the same conditions as set forth in Example 1. Diethyl oxalate was hydrogenated in the reaction tube under the various reaction conditions shown in Table 9.

TABLE 9

| | Reaction conditions | | | | | Results | | |
|---|---|---|---|---|---|---|---|---|
| Example | Temperature (°C.) | Pressure (kg/cm² · G) | SV (hr⁻¹) | LHSV (g/ml · hr) | Mole ratio of hydrogen/ diethyl oxalate | Conversion of diethyl oxalate (%) | Selectivity to ethylene glycol (%) | Selectivity to ethyl glycollate (%) |
| 11 | 225 | 0 (atmospheric) | 5300 | 0.11 | 315 | 100 | 62.7 | 37.0 |
| 12 | 195 | 3 | 1400 | 0.024 | 383 | 100 | 87.0 | 0 |
| 13 | 210 | 3 | 5550 | 0.083 | 435 | 100 | 95.9 | 0 |
| 14 | 225 | 3 | 5810 | 0.198 | 213 | 100 | 85.4 | 11.3 |

The above examples demonstrate that when the hydrogenation catalyst of this invention is used in the hydrogenation of the oxalate, the oxalate reacts at a high conversion and the selectivities to ethylene glycol and the glycollate are high.

What we claim is:

1. In a process for producing ethylene glycol by the vapor phase catalytic hydrogenation of a di($C_1$-$C_8$)alkyl ester of oxalic acid in the presence of a catalyst and hydrogen gas, the improvement wherein
   (i) said hydrogenation is carried out at a temperature of about 150° to about 240° C. and a pressure of about 0.5 to about 50 atmospheres for a contact time of about 0.2 to about 6 seconds in a hydrogen/oxalate mole ratio of about 10 to about 500, and
   (ii) said catalyst has the following composition formula $CuMo_kBa_pO_q$ wherein k, p and q represent gram-atom of Mo, Ba and O, respectively, per gram-atom of Cu, each of k and p is a positive number of at least 0.01 such that the sum k+p is up to 1.5, and the k/p ratio is in the range of from 0.8 to 1.2, and q is a number determined depending upon the atomic valences and gram-atoms of Cu, Mo and Ba.

2. The process of claim 1 wherein k=0.01 and p=0.01.
3. The process of claim 1 wherein k=0.06 and p=0.06.
4. The process of claim 1 wherein k=0.1 and p=0.1.
5. The process of claim 1 wherein k=0.2 and p=0.2.
6. The process of claim 1 wherein k=0.5 and p=0.5.
7. The process of claim 1 wherein the dialkyl ester of oxalic acid is diethyl oxalate.
8. The process of claim 7 wherein the conversion of diethyl oxalate is about 100% and the selectivity to ethylene glycol is at least about 74%.
9. A process for producing a glycollic acid ester at high selectivity which comprises carrying out the vapor-phase catalytic hydrogenation of a di($C_1$-$C_8$)alkyl ester of oxalic acid at a pressure of about 0.5 to about 3 atmospheres, and at a temperature in the range from about 150° to 240° C. for a contact time of about 0.2 to about 6 seconds in the presence of hydrogen and a hydrogenation catalyst composition selected from the group consisting of:

$CuMo_{0.2}Ba_{0.01}O_q$ and $CuMo_2Ba_2O_q$ wherein q is a number determined depending upon the atomic valences and gram-atoms of Cu, Mo and Ba.

10. The process of claim 9 wherein the hydrogenation catalyst has the formula $CuMo_2Ba_2O_q$ and wherein the reaction temperature is in the range of from about 210° C. to about 240° C., the reaction pressure is about 1 atmosphere and the contact time is in the range of from about 1.5 to 3.0 g.second/ml.
11. The process of claim 9 wherein the hydrogenation catalyst is $CuMo_{0.2}Ba_{0.01}O_q$ wherein the reaction pressure is about 1 atmosphere, the reaction temperature is in the range of from about 185° to 190° C. and the contact time is about 1.5 g.second/ml.

* * * * *